United States Patent
Ripart et al.

(10) Patent No.: US 7,856,276 B2
(45) Date of Patent: Dec. 21, 2010

(54) REMOTE SUPPORT SYSTEM FOR PROGRAMMING ACTIVE IMPLANTABLE MEDICAL DEVICES SUCH AS CARDIAC PACEMAKERS, DEFIBRILLATORS, CARDIOVERTORS OR MULTISITE DEVICES

(75) Inventors: Alain Ripart, Gif-sur-Yvette (FR); Richard Poulet, Montrouge (FR)

(73) Assignee: Ela Medical S.A.S., Montrouge (FR)

( * ) Notice: Subject to any disclaimer, the term of this patent is extended or adjusted under 35 U.S.C. 154(b) by 1234 days.

(21) Appl. No.: 10/435,496

(22) Filed: May 9, 2003

(65) Prior Publication Data
US 2004/0010297 A1    Jan. 15, 2004

(30) Foreign Application Priority Data
May 17, 2002   (FR) .................................. 02 06072

(51) Int. Cl.
*A61N 1/00* (2006.01)
(52) U.S. Cl. ........................................................ 607/60
(58) Field of Classification Search .................. 607/60, 607/30, 32; 600/510, 509; 709/230; 128/903, 128/904; 359/724, 726, 727, 641, 642, 737; 705/2; 370/430
See application file for complete search history.

(56) References Cited

U.S. PATENT DOCUMENTS

| | | | | |
|---|---|---|---|---|
| 3,701,851 A | * | 10/1972 | Starrett | 370/430 |
| 5,012,814 A | * | 5/1991 | Mills et al. | 600/510 |
| 5,586,556 A | * | 12/1996 | Spivey et al. | 600/510 |
| 5,619,183 A | | 4/1997 | Ziegra et al. | 340/505 |
| 5,752,976 A | * | 5/1998 | Duffin et al. | 607/32 |
| 5,941,829 A | * | 8/1999 | Saltzstein et al. | 600/509 |
| 6,363,282 B1 | * | 3/2002 | Nichols et al. | 607/30 |
| 6,598,084 B1 | * | 7/2003 | Edwards et al. | 709/230 |

(Continued)

FOREIGN PATENT DOCUMENTS

EP    0 856 333 A2    8/1998

(Continued)

*Primary Examiner*—George Manuel
(74) *Attorney, Agent, or Firm*—Orrick Herrington & Sutcliffe, LLP

(57) ABSTRACT

A remote support system for programming active implantable medical devices such as cardiac pacemakers, defibrillators, cardioverters or multisite devices. A station is equipped with a programmer that is able to read, by telemetry, information stored in an implantable device, and transmit over a telephone line the information thus read, namely patient data and/or internal parameters for operating the programmer or programming parameters of the implant. A remote analysis station is configured to receive the information sent on the telephone line and display and/or analyze the transmitted information. The programmer includes an input to collect a voice signal and a multiplexor so that the data and/or parameters and the voice signal collected, are simultaneously delivered at the multiplexor output in real-time as a multiplexed signal that, in turn, is applied to a tele-transmission circuit (e.g., a modem). The analysis station includes a circuit to restore the audio and a demultiplexor to both receive the signal on the telephone line and deliver to the separate output channels the data and/or parameters and the aforementioned voice signal. The data and/or parameters delivered by the multiplexor are applied to a display and/or an analysis circuit to analyze the patient data, and the voice signal is applied to a restitution circuit to provide an audio signal, enabling bidirectional real-time voice communications over the same transmission line carrying the patient data.

7 Claims, 1 Drawing Sheet

U.S. PATENT DOCUMENTS

| | | | |
|---|---|---|---|
| 6,704,602 B2 * | 3/2004 | Berg et al. | 607/60 |
| 2001/0037366 A1 | 11/2001 | Webb et al. | 709/204 |
| 2002/0026103 A1 | 2/2002 | Norris et al. | 600/300 |
| 2002/0026223 A1 | 2/2002 | Riff et al. | 607/27 |
| 2004/0128161 A1 * | 7/2004 | Mazar et al. | 705/2 |

FOREIGN PATENT DOCUMENTS

EP     0 856 333 A3     8/1998

* cited by examiner

REMOTE SUPPORT SYSTEM FOR PROGRAMMING ACTIVE IMPLANTABLE MEDICAL DEVICES SUCH AS CARDIAC PACEMAKERS, DEFIBRILLATORS, CARDIOVERTORS OR MULTISITE DEVICES

FIELD OF THE INVENTION

The present invention relates to "active implantable medical devices" as defined by the Jun. 20, 1990 Directive 90/385/CE of the Council of the European Communities. This definition includes cardiac pacemakers, defibrillators, cardiovertors and/or multisite devices, but also neurological apparatuses, medical substance diffusion pumps, cochlear implants, implanted biological sensors, etc., as well as the devices for the measurement of pH or the measurement of intracorporal impedance.

BACKGROUND OF THE INVENTION

Active implantable medical devices, hereafter simply called "implants", typically have a data memory to store information that can be read by use of an external programmer employing telemetry techniques that are in themselves well-known. The external programmer (or more commonly, the "programmer") is associated with a microcomputer at the disposal of the physician and includes a display screen, a telemetry head for communicating with an implant, a keyboard and mouse (or other user interface) for the input of control parameters and the data, as well as various circuits for memorizing and processing of data (e.g., data acquired by the implant).

The physician, who is a user of the programmer, is a specialized doctor with access to information, namely the patient data and the operating parameters, that is stored in the memory of the implant. This include information consists of, among other things the various "programming" controls, including, for example, the controls to modify the setting parameters, and, thus, the operation of the pacemaker.

The starting point of the present invention is the observation that, very often, the physician-user of the programmer needs to question an expert, for example, to be able to choose the most suitable adjustments for the programmer and/or the implant. This need is even more important with the most advanced devices that have a wide variety of adjustments and are not always easy to choose and to parameterize in a way most appropriate for each patient.

To satisfy this particular need, it is known, for example, from EP-A-0 856 333 (assigned to Ela Medical SpA) how to implement a connection between the station where the physician sits and the distant site where the expert is, with several lines, including:

a first line for the transmission of the parameters from the pacemaker towards the distant site, a second line for the establishment of a bidirectional voice communication between the physician and the expert, and a third line for the possible transmission, in real time, of a surface electrocardiogram. Experience has indeed shown that a voice connection is absolutely essential for effective remote support because data transmission on its own, even when accompanied by messages in the form of short text, is insufficient to obtain satisfactory help. Such help generally requires a total interactivity between the physician's observations and handling of the advice, and the advice given by the expert providing remote support.

One of the problems with this solution, however, is that in practice this proposal requires two, or even three, distinct telephone links, and thus is difficult to implement in a hospital environment. Indeed, in general, electrophysiology rooms currently have only one telephone line, which would require either equipping each particular room with a second line, an expensive proposition, or making the connection using a second line located in another room, which, of course, is inconvenient.

Because of the constraints found in the hospital environment, it is not possible to use for the voice connection a wireless or mobile (cell) telephone. The use of these apparatuses is prohibited in hospitals because of the risks of disturbing the surrounding equipment with the powerful electromagnetic signals produced by these telephones.

OBJECTS AND SUMMARY OF THE INVENTION

It is, therefore, an object of the present invention to solve this difficulty by proposing a remote support system making it possible for the operator of a programmer to contact and maintain a permanent telephone conversation with an expert, and to transmit data and/or parameters for adjusting the programmer to take a certain action (e.g., a query command which provokes a certain response) or for programming the implant, whereby the transmission would not interfere with the conversation because it would be using, without modification, the infrastructures generally available in the current electrophysiology rooms.

The tele-transmission of data coming from an implantable medical device such as a cardiac pacemaker by the intermediary of a telephone links in itself is well-known. See, for example, DE-A-44 01 443 or U.S. Pat. No. 5,586,556, where the data are digitized and converted into audio signals transmitted by a telephone headset to a distant site.

However, in these known techniques, although the physician uses a programmer, there is no teaching of remote expert support being brought to a physician. Rather, the disclosure teaches a system for both remote monitoring of the disposition of an isolated patient, and remote reprogramming, if necessary, of the pacemaker (remote handling by the physician). In other words, these known techniques are intended for use with isolated patients usable in all places but a doctor's office or an electrophysiology room in a hospital or clinic.

The system for remote support of the invention is of the general type described by the EP-A-0 856 333 mentioned above. Such a system includes, on the one hand, a station equipped with a programmer and, on the other hand, a distant analysis station, the station and the analysis station being connected by a single telephone link. The programmer of the station includes means for reading by telemetry a data memory of the implanted device, and means for tele-transmitting towards the distant site the aforesaid read data and/or internal parameters of the programmer, these means for tele-transmission being coupled with the aforementioned telephone line.

The distant analysis station includes means for receiving the data sent on the telephone line by the means for tele-transmitting, and means for displaying and/or analyzing of the data thus transmitted.

According to the invention, the programmer also comprises means for collection and digitization of a voice signal, and a multiplexor able to receive at a first input the aforementioned data read and/or parameters of the programmer and at a second input the collected and digitized voice signal, wherein the multiplexer is further able to deliver at the output a multiplexed signal applied to the means for tele-transmitting. As for the analysis station, it includes a circuit of restitution of audio signals from the digitized voice signals transmitted, and a demultiplexor able to receive at its input the signal received on the telephone line and able to deliver at a first output the aforementioned data read and/or internal parameters, and at a second output, the aforementioned voice signal. The data read and/or internal parameters delivered by the multiplexor/demultiplexor system can be applied to the aforementioned means for display and/or analysis of the data, and the voice signal is applied to the circuit of restitution of the audio signals.

BRIEF DESCRIPTION OF THE DRAWING

Further features, advantages and characteristics will become apparent to a person of ordinary skill in the art in view of the following discussion made with reference to the drawing annexed, which is a schematic representation of a system in accordance with a preferred embodiment of the invention.

DETAILED DESCRIPTION OF THE INVENTION

Figure 1:
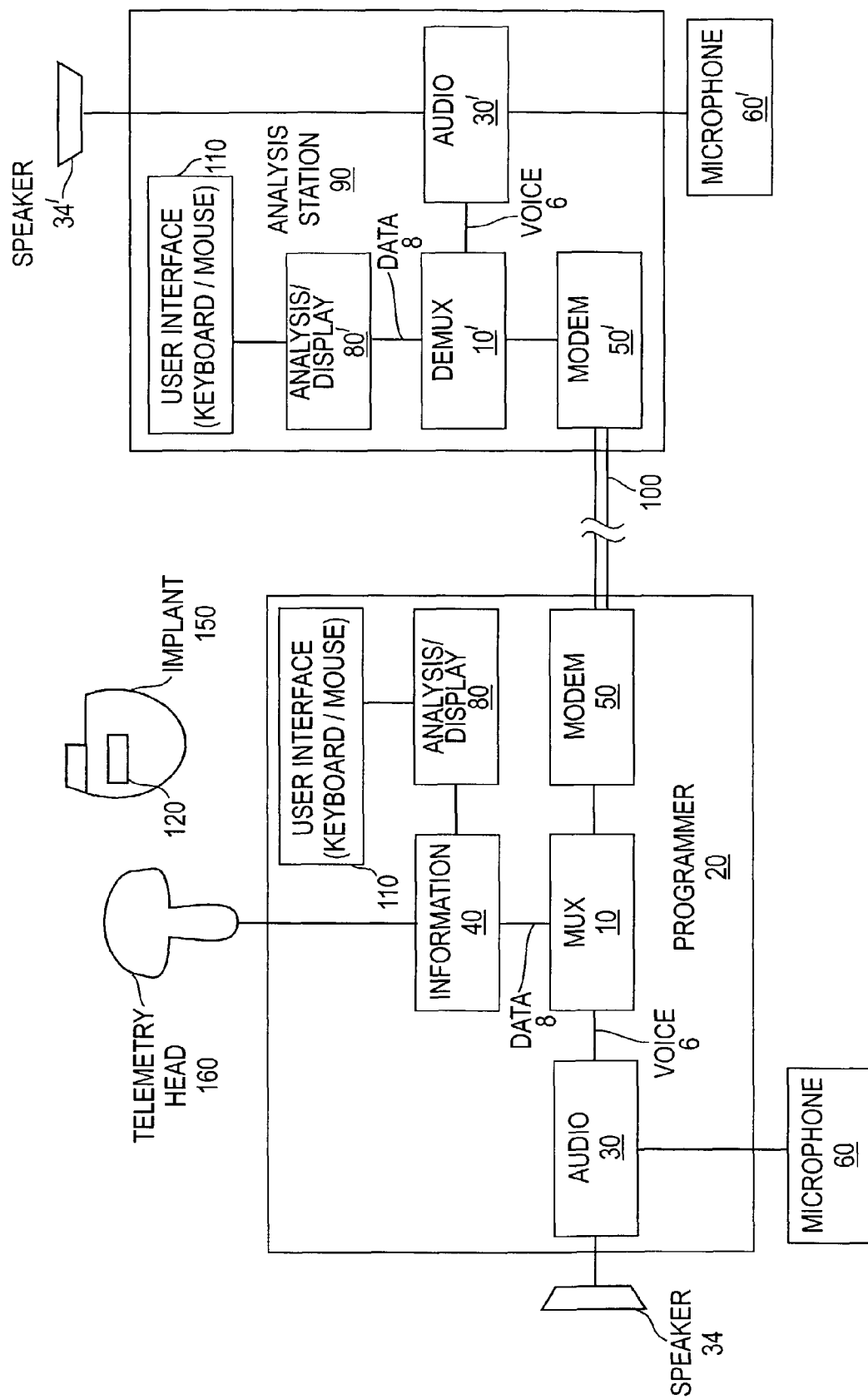

With reference to the drawing figure, the invention can, in a preferred embodiment, be implemented by integrating a multiplexor circuit 10 into a preexistent programmer 20. An example of a programmer in particular use for this purpose is the Orchestra™ brand programmer marketed by Ela Médical, Montrouge, France. This commercial programmer apparatus, in addition to having a conventional head 160 with an antenna and acquisition or information circuit 40 for reading an implant by telemetry, and a modem 50 for the tele-transmission of the data, integrates a microphone 10 and an audio circuit 30 (otherwise used, for example, for controlling the programmer by voice command).

The multiplexor circuit 10 is a circuit of a known type making it possible to multiplex data and voice. One suitable device, for example, is that similar to the Model AR80 apparatus manufactured by Digicom SpA, which are apparatuses known to be suitable for multiplexing or demultiplexing several channels of information over the same one telephone line 100, typically a common two or four wire telephone line having at least one data channel 8 and one voice channel 6. The operation of the device 10 is symmetrical (i.e., it is bidirectional because it can be assembled to operate as both a multiplexor and a demultiplexor), and it automatically manages the corrections of errors and the optimization of the band-width in a known manner. The multiplexing can be performed in mode TDM (temporal division), SDM (statistical division), or any other mode equivalent or derived from the latter.

Analysis station 90 includes a modem 50' that communicates with programmer modem 50 in a conventional manner to effect the tele-transmission, a demultiplexor 10' which is compatible with programmer multiplexor 10 and also is bidirectional for separating the tele-transmitted multiplexed data into separate voice channel 6 and data channel 8. The voice channel 6 is provided to audio circuit 30' which comprises a restitution circuit to restore the transmitted voice information to audio signals that can be projected through a speaker 34 (or ear phones, etc.). A microphone 60 also is provided to enable voice communication from the expert at analysis station 90 to the physician at programmer 20. The data channel 8 is coupled to analysis/display circuit 80 where the expert can analyze and view the tele-transmitted information, which includes, for example, the control parameters (of the implant or the programmer) or patient specific data stored in a memory 120 of a remote implant 150, as read by telemetry head 160 of programmer 20. The analysis station 90, similar to the programmer 20, has a user interface 110 (e.g., a keyboard, mouse or mouse equivalent, joystick or touch screen), to manipulate data display or conduct an analysis of the information teletransmitted, as known in the art.

It is thus possible to simultaneously transmit voice and data signals on a single telephone line 100 in an entirely transparent way for the two users, namely the physician and the expert. It should be understood that the single transmission line can include a wireless component.

One skilled in the art will appreciate and understand that the specific embodiments disclosed herein are presented for purposes of illustration, and not of limitation, and that constructions and circuits and communication protocols other than those disclosed herein may be used as well.

We claim:

1. A system for remote support for the programming of an active implantable medical device having a memory for storing information selected from among patient data and an internal control parameter, comprising:
    a station equipped with a programmer, a distant analysis station, and a telephone link connecting the station and the analysis station;
    wherein the programmer of the station comprises:
        means for reading by telemetry the information stored in said device,
        means for tele-transmitting said read information towards the distant analysis station,
        means for collecting and digitizing a voice signal, and
        a multiplexor having a first input to receive the information read from said memory, a second input to receive the voice signal simultaneously with said information read from said device, and an output to provide a multiplexed signal multiplexing the first input and the second input to the means for tele-transmitting,
    wherein said means for tele-transmitting is coupled with said telephone line, said means for collecting and digitizing a voice signal, and said multiplexor;
    wherein the distant analysis station comprises:
        means for receiving said tele-transmission of said information over said telephone line;
        a demultiplexor having an input to receive the multiplexed signal over the telephone line, a first output to deliver said information and, and a second output to deliver the voice signal simultaneously with said information,
        means responsive to the first output of the demultiplexor for displaying and/or analyzing of the information thus transmitted, and
        a circuit responsive to said voice signal at said second output of the demultiplexor to restore audio signal; and
    wherein the multiplexor and the demultiplexor cooperate to provide bidirectional voice communications over said telephone line in real-time.

2. The apparatus of claim 1, wherein the multiplexed signal is provided in a temporal division mode (TDM).

3. The apparatus of claim 1, wherein the multiplexed signal is provided in a statistical division mode (SDM).

4. An apparatus for programming an active implantable medical device having a memory, comprising:
    a data acquisition circuit for acquiring by telemetry data stored in the memory of the active implantable medical device;
    an audio circuit for collecting and digitizing a voice signal;

a multiplexor coupled to the data acquisition circuit and the audio circuit for multiplexing the voice signal and the data to generates a multiplexed signal; and a modem coupled to the multiplexor for transmitting the multiplexed signal onto a telephone link in real-time, said telephone link being connectable to a distant analysis station.

5. The apparatus of claim 4, wherein said modem receives signals over said telephone link in real-time, further comprising:

a programming circuit coupled to the modem for identifying in said received signals a control signal; and a telemetry head coupled to said programming circuit for transmitting said control signal by telemetry to said active implantable medical device, thereby programming said memory.

6. An apparatus for communicating with a programmer, comprising:

a modem for receiving a multiplexed signal from the programmer over a telephone line in real-time, wherein the multiplexed signal comprises a digitized voice signal and data;

a demultiplexor coupled to the modem for demultiplexing the multiplexed signal to restore the digitized voice signal and the data;

an audio circuit coupled to the demultiplexor for generating an audio signal from the digitized voice signal;

an analysis circuit coupled to the demultiplexor for analyzing the data to produce analyzed data; and a display coupled to the analysis circuit for displaying the analyzed data, wherein the programmer communicates with an active implantable medical device having a memory for storing information selected from among patient data and an internal control parameter.

7. The apparatus of claim 6 further comprising:

a user interface for providing the analyzed data to an operator;

an input device for receiving an input from the operator;

a signal processor coupled to the input device for producing a control signal from the input, wherein modem transmits the control signal to the programmer over the telephone line in real time.

* * * * *